(12) United States Patent
Terlecki (10) Patent No.: US 9,375,314 B2
(45) Date of Patent: Jun. 28, 2016

(54) PROSTHETIC PENILE IMPLANTS WITH TETHERED REAR TIP EXTENDERS AND RELATED METHODS

(71) Applicant: Wake Forest University Health Sciences, Winston-Salem, NC (US)

(72) Inventor: Ryan P. Terlecki, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 37 days.

(21) Appl. No.: 14/312,999

(22) Filed: Jun. 24, 2014

(65) Prior Publication Data

US 2015/0011823 A1    Jan. 8, 2015

Related U.S. Application Data

(60) Provisional application No. 61/841,959, filed on Jul. 2, 2013.

(51) Int. Cl.
*A61F 2/26* (2006.01)

(52) U.S. Cl.
CPC ........... *A61F 2/26* (2013.01); *A61F 2230/0065* (2013.01); *A61F 2240/004* (2013.01); *Y10T 29/49826* (2015.01)

(58) Field of Classification Search
CPC ................... B65D 55/16; B65D 55/51–55/24; B65D 41/16; B65D 41/41; B65D 41/48; A61F 2/26
USPC ...................................................... 600/38–41
See application file for complete search history.

(56) References Cited

U.S. PATENT DOCUMENTS

| | | | | |
|---|---|---|---|---|
| 3,965,890 A | * | 6/1976 | Gauthier | A61B 17/0293 403/79 |
| 4,411,260 A | * | 10/1983 | Koss | A61F 2/26 600/40 |
| 4,753,358 A | * | 6/1988 | Virca | B01L 3/50825 215/230 |
| 5,090,583 A | * | 2/1992 | Hoffman | B65D 47/147 215/250 |
| 6,808,489 B2 | | 10/2004 | George et al. | |
| 7,985,176 B1 | * | 7/2011 | Morningstar | A61F 2/26 600/40 |
| 8,343,033 B2 | * | 1/2013 | Daniel | A61F 2/26 600/40 |

OTHER PUBLICATIONS

AMS Ambicor®, 2-Piece Inflatable Penile Prosthesis, Product Overview, http://www.americanmedicalsystems.com, date unknown but believed to be before the priority date of the present application, printed from the internet Apr. 16, 2013, 2 pages.
AMS CXR Rear Tip Extender (RTE) Kit, Instructions for Use, 2010, 15 pages.
Simmons et al., Penile Prosthesis Implantation: Past, Present and Future, International Journal of Impotence Research, 2008, p. 437-444, vol. 20.

* cited by examiner

*Primary Examiner* — Samuel Gilbert
(74) *Attorney, Agent, or Firm* — Myers Bigel & Sibley, P.A.

(57) ABSTRACT

Rear tip extenders include a tether attached to a collar that can be mounted onto a respective cylinder forward of a fluid line (that communicates with a scrotal pump) to prevent full separation or detachment from the cylinder during a revision procedure.

24 Claims, 10 Drawing Sheets

PROSTHETIC PENILE IMPLANTS WITH TETHERED REAR TIP EXTENDERS AND RELATED METHODS

RELATED APPLICATIONS

This application claims the benefit of and priority to U.S. Provisional Application Ser. No. 61/841,959 filed Jul. 2, 2013, the contents of which are hereby incorporated by reference as if recited in full herein.

FIELD OF THE INVENTION

This invention relates to prosthetic penile implants.

BACKGROUND OF THE INVENTION

Figure 1:
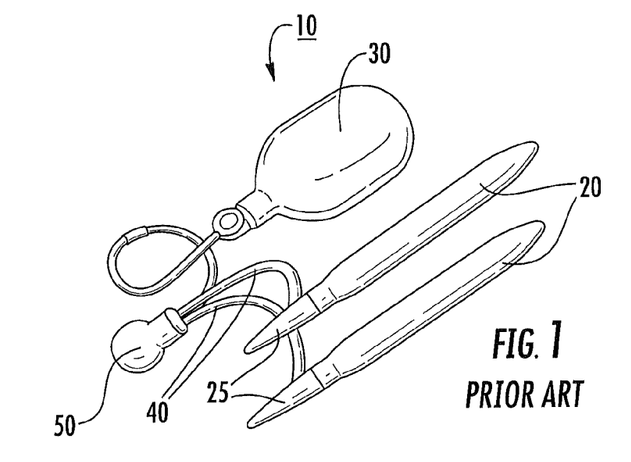
FIG. 1 is a top perspective view of an exemplary three-piece prior art prosthetic implant.
Figure 2:
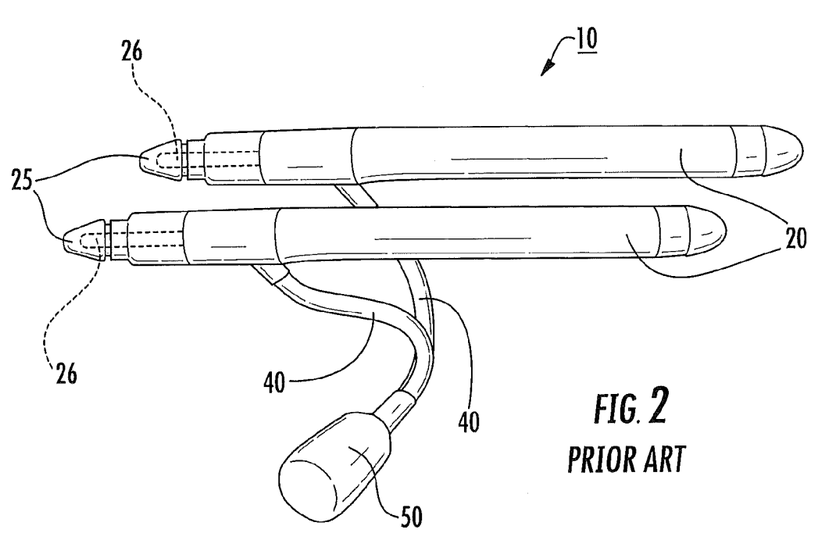
FIG. 2 is a side perspective view of an exemplary two-piece prior art prosthetic implant.

Prosthetic penile implants have been used for many years to allow men with erectile dysfunction to achieve erection. Penile implants are available as inflatable or non-inflatable devices. Inflatable penile prostheses are available in two- and three-piece configurations. Each of the so-called two and three piece configurations have a pair of elongate intracorporeal cylinders 20 (which are counted as a single one of the two or three component systems) and a scrotal pump 50. Typically, the cylinders 20 of such a prosthetic device are implanted into the corpus cavernosae and the pump 50 is implanted in the scrotum (e.g., a scrotal pump). The three-piece configuration, an example of which is shown in FIG. 1, has a separate reservoir 30 that connects via tubing to the scrotal pump 50. The reservoir 30 is typically implanted in the abdomen, pelvis, or in an ectopic location under the abdominal wall. The two-piece configuration, an example of which is shown in FIG. 2, does not require the separate reservoir. Instead, the two-piece configuration uses rear tip cylinder reservoirs 26 that transfer fluid into center cylinder chambers 20 which, once full, do not expand, but the fluid in the center chambers pressurize to provide penile rigidity. A commercially available, two-piece inflatable penile prostheses is the AMS Ambicor® from American Medical Systems (AMS). Different models of a three-piece inflatable penile prosthesis are available from AMS and Coloplast Corporation, MN, the latter including the Titan™ inflatable prosthesis.

An inflatable penile prosthesis can be implanted so that a respective cylinder is inserted into the corpus cavernosum with the proximal end of the cylinder (the rear tip) residing toward the pubic bone.

To achieve a proper fit, the surgeon may select one or more rear tip extenders (RTEs) 25 of a suitable length to attach onto the rear of the cylinder. The RTE may be in the form of cap (e.g., a silicone rubber cap) that fits onto the rear of the cylinder to extend the length a suitable amount. In some cases, more than one RTE is attached to the rear end of the cylinder 20. In any event, typically, these RTEs are attached to the rear end of the cylinder via friction fit and separation of the components is inhibited by a vacuum that results when they are pulled in opposite directions.

SUMMARY OF EMBODIMENTS OF THE INVENTION

Embodiments of the invention provide a rear tip extender that is tethered to a collar that can be mounted onto a respective cylinder in front of a fluid line to and from a scrotal pump to prevent full separation or detachment from the cylinder during a revision procedure.

Embodiments of the invention are directed to rear tip extender assemblies for a penile prosthesis implant. The RTE assemblies include: a rear tip extender and/or rear tip cap sized and configured to attach to an elongate cylinder of a penile prosthesis implant; a collar that is sized and configured to reside against an outer surface of the cylinder; and at least one tether that is attached to the rear tip extender and the collar.

The rear tip extender can be a rear tip cap.

The rear tip cap can be formed of silicone rubber.

The collar and rear tip extender can include an elastomeric material and the tether can be integrally moldably attached to at least one of the collar and rear tip extender.

The tether can be integrally moldably attached to both the collar and rear tip extender.

The tether can be a single tether and the collar and tether can have an integral monolithic configuration that is sized and configured to slidably travel over a forward end of the cylinder and, in position, can reside in front of and proximate to a fluid line that extends outward from a rear portion of the cylinder.

The collar can include at least one substantially arcuate longitudinally extending recess.

The collar can include a plurality of circumferentially spaced apart substantially arcuate recesses.

The rear tip extender assembly can be in combination with at least one other rear tip extender assembly and rear tip assembly can have a different length rear tip extender.

Other embodiments are directed to penile prosthesis implants. The implants include: (a) an elongate cylinder having longitudinally opposing front and rear end portions, the rear end portion comprising a fluid conduit junction; (b) a collar on the cylinder residing adjacent to the fluid conduit junction; (c) a rear tip extender attached to the rear end portion of the cylinder; and (d) at least one tether attached to the collar and the rear tip extender.

The rear tip extender can be a rear tip cap.

The rear tip cap and at least one tether can be of silicone rubber.

The collar and the rear tip extender can be formed of an elastomeric material and the at least one tether can be integrally moldably attached to at least one of the collar and rear tip extender.

The at least one tether can be a single tether that is integrally moldably attached to both the collar and rear tip extender.

The collar can be a single, monolithic member that is sized and configured to slidably travel over a forward end of the cylinder to reside adjacent the fluid junction.

The collar can include at least one substantially arcuate longitudinally extending recess.

Yet other embodiments are directed to methods of configuring a penile prosthesis implant for insertion into a patient. The methods include: (a) providing a pair of elongate cylinders with longitudinally opposing front and rear end portions, the rear end portions having a fluid junction with a fluid line extending away from the cylinder and a rear end; (b) sliding a collar having a longitudinally extending tether attached to a rear tip extender over a front end portion of each respective cylinder to a position adjacent the fluid line junction; and (c) placing a rear tip extender on the rear end of the cylinder thereby tethering the rear tip extender to the collar.

Yet other embodiments are directed to methods of fabricating a penile implant, including: (a) providing a mold with a mold cavity configured to define three attached members of defined shape, including a rear tip extender, a collar and a tether attaching the rear tip extender and collar; and (b) flowably introducing moldable material into the mold cavity to form the collar, rear tip extender and attached tether as a molded assembly.

Embodiments of the invention include providing instructional media showing the method of configuring a penile prosthesis implant for insertion into a patient.

The foregoing and other objects and aspects of the present invention are explained in detail in the specification set forth below.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DESCRIPTION OF EMBODIMENTS OF THE INVENTION

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments. The term "distal" refers to a direction or location that is closer to or toward a patient while the term "proximal" refers to the opposing direction or a location that is further away from the patient.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein.

The term "tether" refers to a flexible or semi-rigid member that extends between and attaches two separate components.

The term "about" means that the recited number or value can vary by ±20%.

The term "sterile" means that the noted device or material meets or exceeds defined medical guidelines of cleanliness and is substantially (if not totally) without contaminants so as to be suitable for medical uses.

The term "semi-rigid" means that the implant is flexible but has sufficient rigidity to substantially maintain its three-dimensional shape under normal loading in the body.

The term "instructional media" refers to electronic and/or paper manuals, videos, user guides, or the like illustrating and/or describing pre-surgical assembly steps and/or a surgical procedure using the tethered penile implant.

Referring now to the figures, FIGS. 3-6 illustrate a cylinder 20 of an inflatable penile implant 10 (FIG. 1, 2) according to embodiments of the present invention. The cylinder 20 has longitudinally opposing front (forward) and rear end portions 20$f$, 20$r$. As shown, a collar 60 resides on the cylinder 20 on the rear end portion 20$r$ proximate a fluid junction 40$j$ at which junction the flexible tube or conduit 40 extends to connect the scrotal pump 50 (FIGS. 1, 2). The collar 60 includes at least one attached tether 70 that is also attached to the rear extender tip 25. The tether 70 can be a single longitudinally extending tether or may be a plurality of longitudinally extending, circumferentially spaced apart tethers (not shown).

The tether 70 is typically attached to or integrally formed onto a wall or the outer surfaces of both the collar 60 and the RTE 25. Although shown in most embodiments as a single tether, more than one tether may be used.

The tether 70 can comprise a thread, strap, suture, wire or other elongate member. The tether 70 can be flexible. The tether 70 can be semi-rigid. The tether 70 can be an integrally molded component of the collar 60.

The collar 60 can be a unitary monolithic component of suitable medical grade material. The collar 60 can comprise silicone rubber or other medical grade suitable elastomeric or polymeric material. The collar 60 can also comprise a biocompatible, non-cytotoxic metal or ceramic. The collar 60 can comprise a combination of materials.

Figure 3:
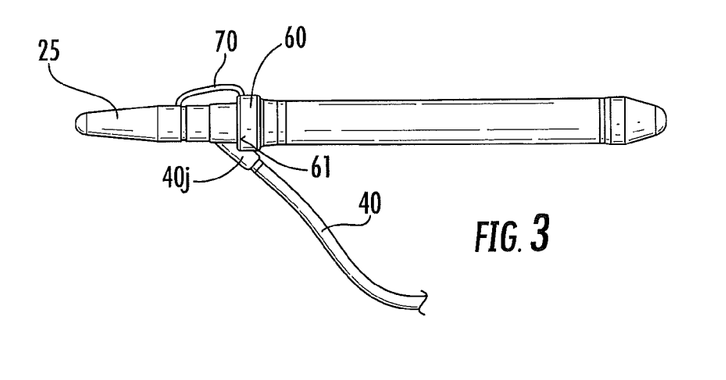
FIG. 3 is a side view of a cylinder with a RTE assembly for a penile implant according to embodiments of the invention.
Figure 4:
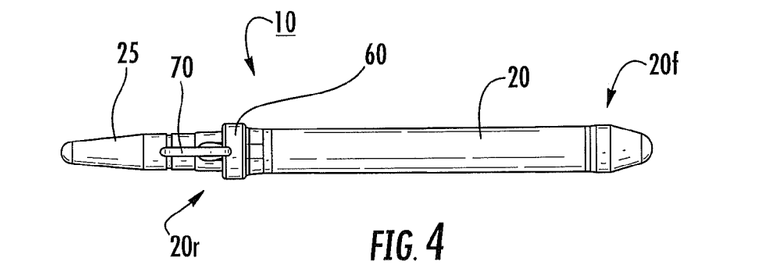
FIG. 4 is a top view of the device shown in FIG. 3.
Figure 5:
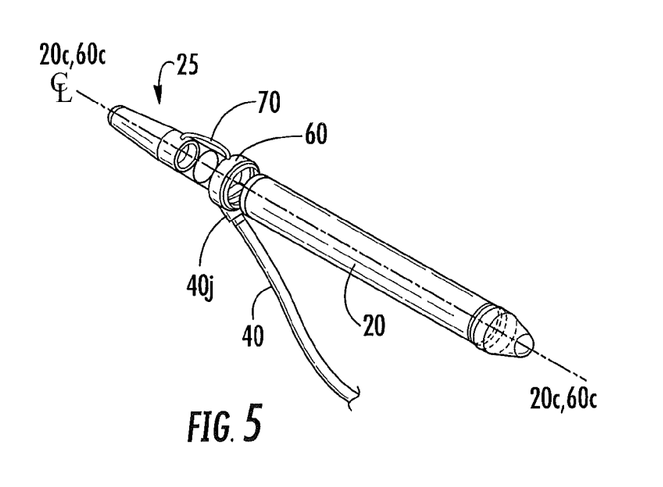
FIG. 5 is a side perspective view of the device shown in FIG. 3.
Figure 6:
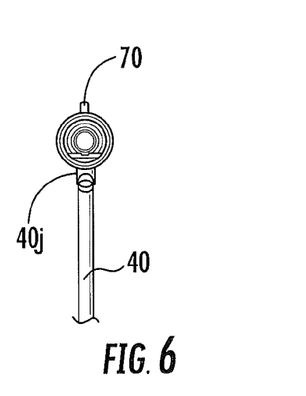
FIG. 6 is an end view of the device shown in FIG. 3.
Figure 7A:
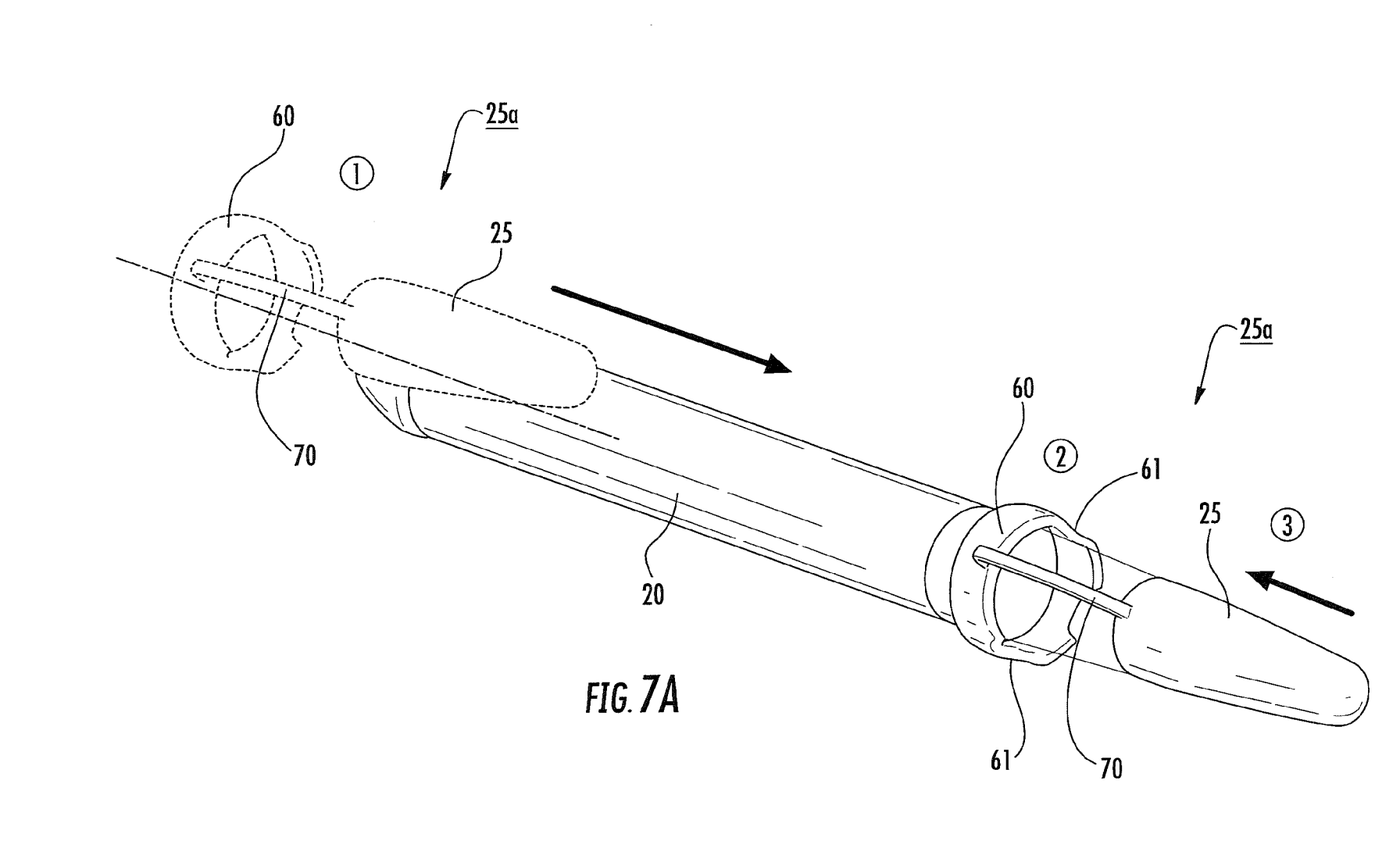
FIG. 7A is an enlarged view of a cylinder illustrating an exemplary assembly procedure for a collar with tether attachment and RTE according to embodiments of the present invention.
Figure 8:
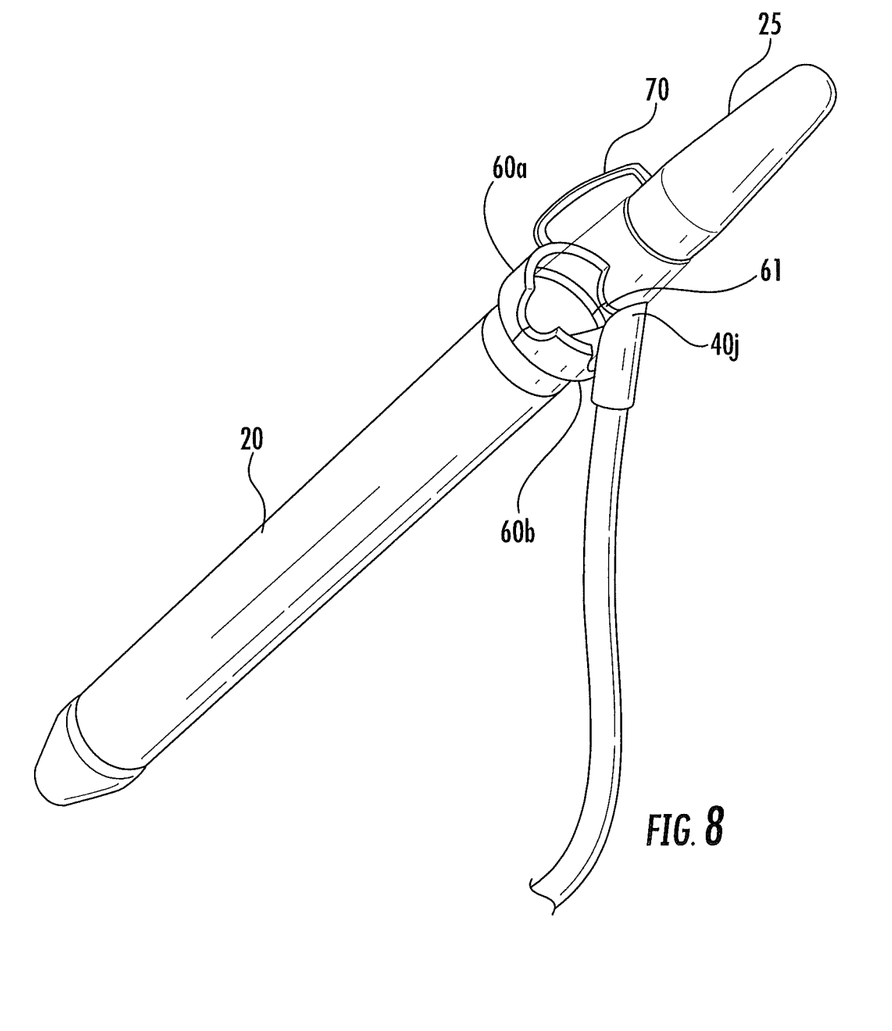
FIG. 8 is an enlarged rear side perspective view of the device shown in FIG. 1 illustrating a two-piece snap fit collar construction according to embodiments of the present invention.

The collar 60 can include at least one arcuate recess 61 (FIGS. 7A, 8). The arcuate recess 61 can be aligned to abut the fluid junction 40$j$ so that the conduit junction or conduit extension 40 resides therein (FIG. 9). The recess 61 can receive the extension 40$j$ which may angle out of the cylinder 20 at about 45 degrees or other angles (FIG. 3).

The collar 60 can be provided in different sizes for different sizes of cylinders 20. The collar 60 can optionally abut the outer surface of the cylinder 20 at the rear end portion 20$r$ or may reside loosely against the outer surface of the cylinder 20 (e.g., so as to not contact at least a portion of the outer wall of the cylinder thereat). The collar 60 can have any suitable axial length and any suitable cross-sectional width and is not required to matably correspond to the cylinder outer diameter. The collar 60 can be between about 0.1 inches to about 0.5 inches in axial length but other lengths may also be suitable.

In some embodiments, the collar 60 can have an axially extending centerline 60$c$ that is concentric with an axially extending centerline 20$c$ of the cylinder 20 as shown in FIGS. 1-6, for example.

Figure 7B:
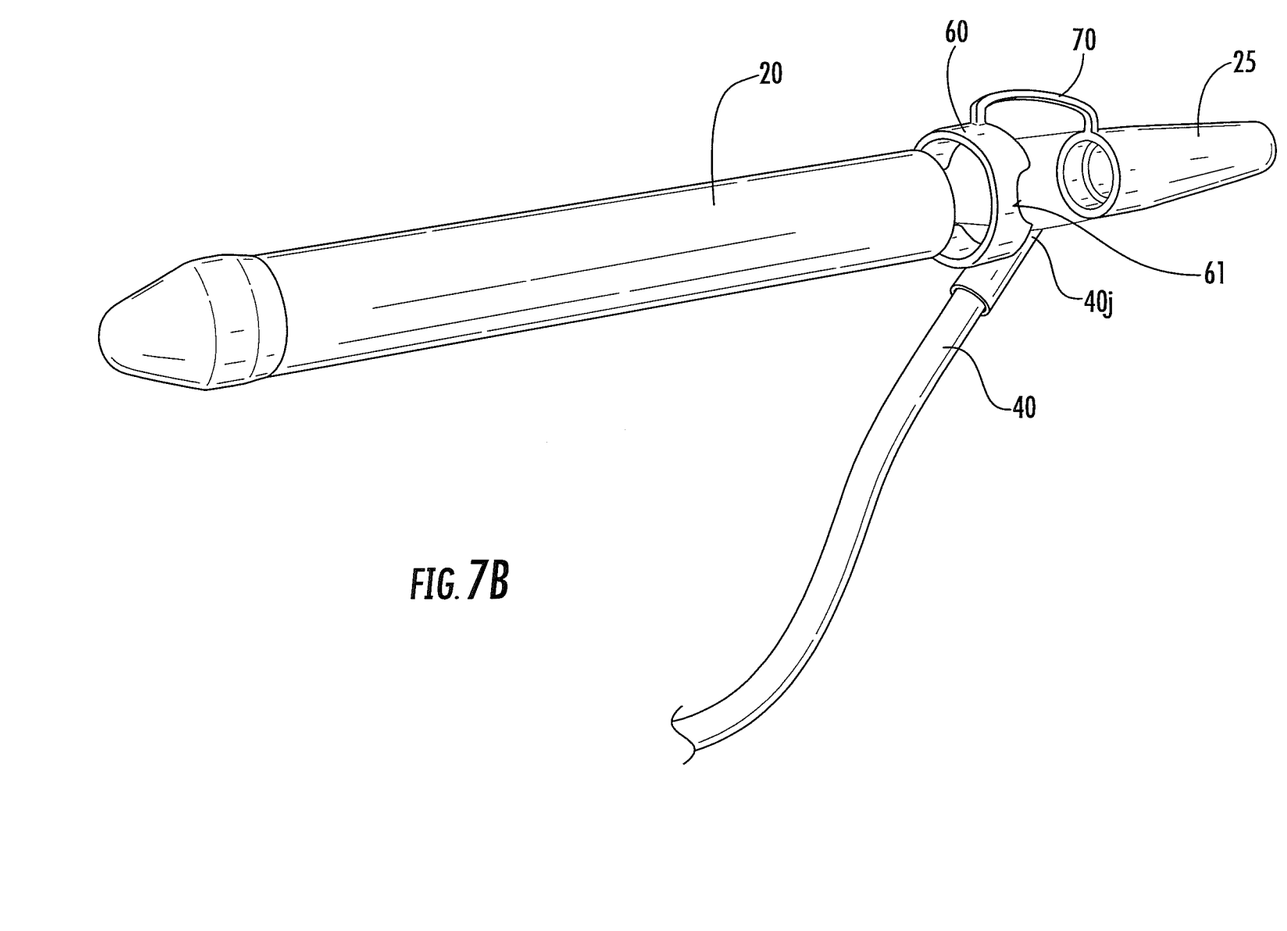
FIG. 7B is an enlarged front perspective view of the device shown in FIG. 3 according to embodiments of the present invention.
Figure 7C:
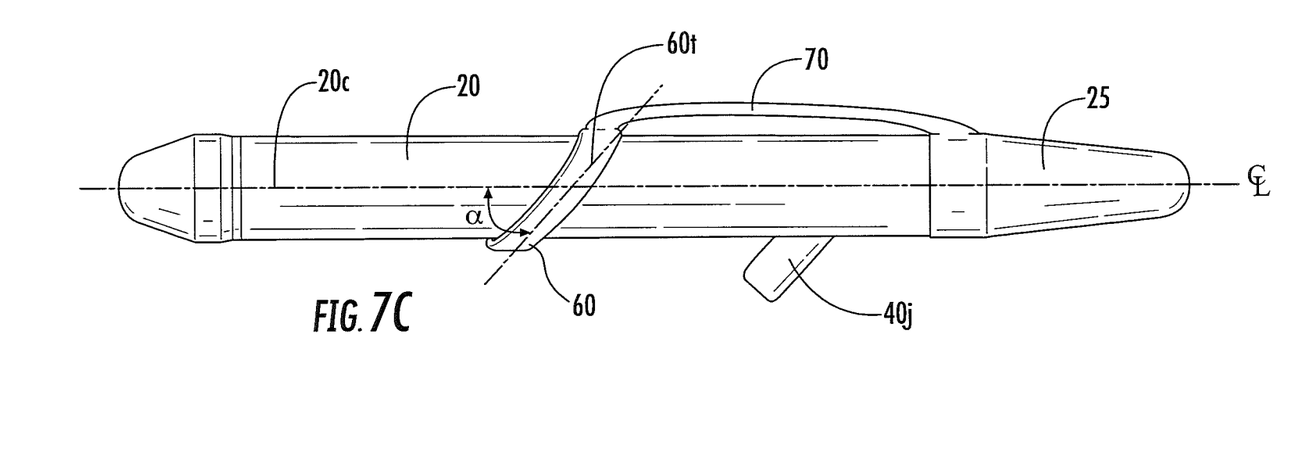
FIG. 7C is a partial side perspective schematic illustration of an alternate embodiment of the collar and tether according to embodiments of the present invention.
Figure 7D:
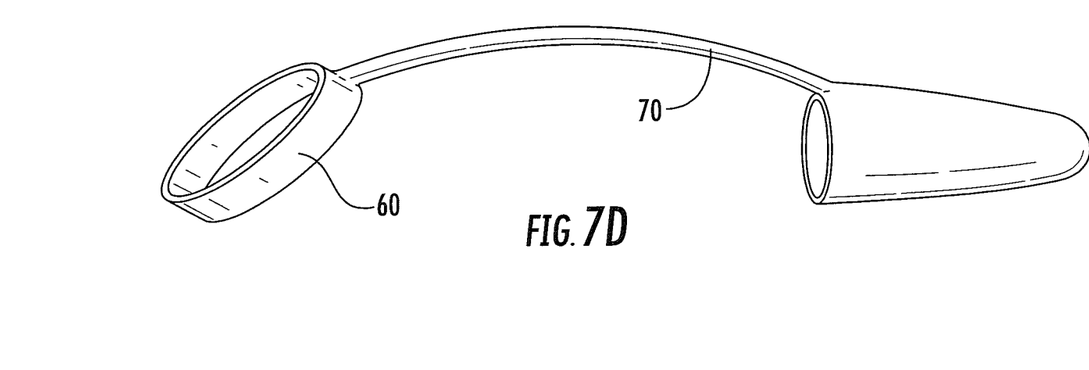
FIG. 7D illustrates the collar and tether embodiment shown in FIG. 7C separate from the implant cylinder.

In some embodiments, as shown in FIG. 7C, the collar 60 can have a transversely extending centerline 60$t$ that angles away from the outer wall of the cylinder so that the centerlines 20$c$, 60$t$ are offset from each other, typically between about 10 degrees to about 75 degrees in either a forward or rearward tilt orientation (shown in FIGS. 7C and 7D as in a rearward tilt orientation).

The collar 60 can be configured to be able to expand in response to inflation/expansion of the cylinders 20 so as not to provide undue compression on the cylinder when in an expanded configuration. The collar 60 can have an accordion, undulated or pleated segment or segments to facilitate expansion and/or may be formed of a resilient, flexible and/or otherwise expandable material.

In some embodiments, the collar 60 can reside loosely against the outer wall of the cylinder and is not required to expand with the expansion of the cylinder 20. The collar 60 can have an inner wall with a cross-sectional width that is 10-50% larger than an outer diameter of the cylinder 20.

The collar 60 can be in the shape of a disk (e.g., with a substantially circular opening). The collar 60 can be in other shapes not requiring a circular opening or circular external outer wall shape. The collar 60 can have any closed geometric shape, e.g., oval, polygonal, triangular and the like.

The tether 70 can have the same material as the collar 60 or the RTE 25 or may comprise a different material. The tether 70 has a length sufficient to extend from at least a front end portion of the RTE 25 to the collar 60; typically, the tether 70 has a length between about 0.5 inches to about 10 inches, typically between about 0.5 inches to about 5 inches. The tether 70 can be longer as it can reside in local tissue and when pulled, it pulls the RTE along with the collar upon a revision or other surgery to provide a positive retention of the two components.

As shown in FIG. 3, for example, the tether 70 can be thin. The tether 70 can have a small width, such as a width that is between about 0.001 inches to about 0.1 inches. In other embodiments, the tether 70 can have a greater width, but if so, the width is typically less than about 40% of the circumference, e.g., between about 1% to about 40% of the circumference. The tether 70 can be configured to reside closely spaced to the body of the cylinder 20 when the RTE 25 and collar 60 are in position on the cylinder 60.

The RTE 25 can be a rear tip end cap (with a closed end tip) as shown in FIGS. 3-6.

Figure 11:
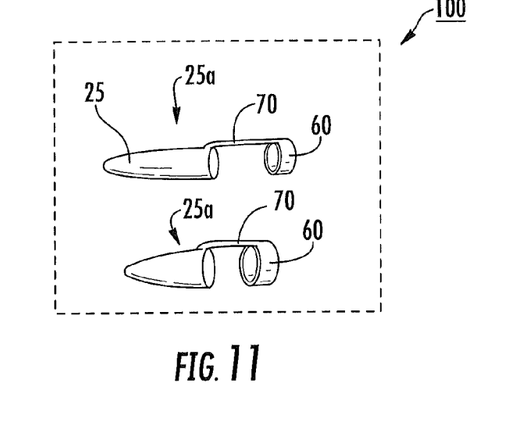
FIG. 11 is a side schematic view of a kit of RTE assemblies according to embodiments of the present invention.

In some embodiments, the collar 60, tether 70 and RTE 25 can be provided pre-assembled as an assembly 25$a$ and provided in a kit 100 of different sizes of RTEs 25 (FIG. 11). The surgeon or other clinician can select an appropriate assembly 25$a$ for use when sizing the patient's anatomical requirements. An assembly 25$a$ can be attached to each respective cylinder 20 prior to placement in a patient.

In some embodiments, the tether 70 is moldably attached to the collar 60 and RTE 25. In some embodiments, the tether 70 is adhesively attached to the respective collar 60 and/or RTE 70. In some embodiments, the collar 60 is mechanically fastened to the tether 70 and/or RTE 70 using, for example, hooks, VELCRO (e.g., loop and hook), or mechanical slide and channel, tongue and groove, rivets, pins or clamp attachment configurations.

Figures 9A, 9B, 10:
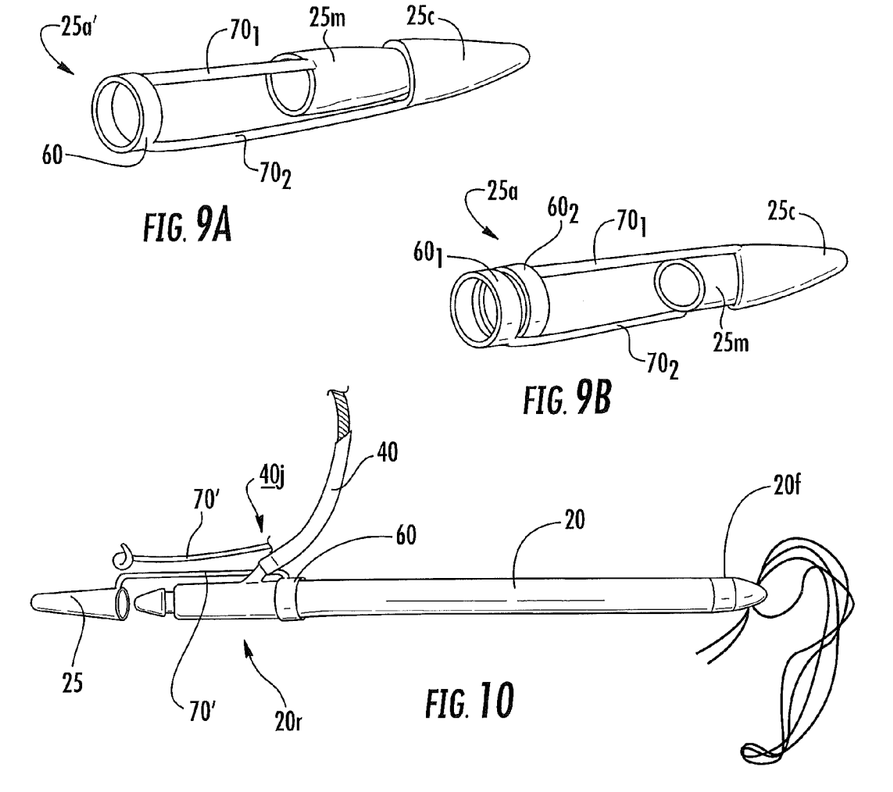
FIG. 9A is a schematic side perspective view of an alternate RTE assembly according to embodiments of the present invention.
FIG. 9B is a schematic illustration to show that two RTE assemblies can be used together according to embodiments of the present invention.
FIG. 10 is a side perspective view of another RTE/collar/tether embodiment according to embodiments of the present invention.

In some embodiments, the assembly 25$a$ includes a single RTE 25 and tether 70 attached to a respective collar 60 as shown, for example, in FIG. 11. In other embodiments, as shown in FIG. 9A, the subassembly 25$a'$ can include the collar 60 attached to two or more RTEs, including a medial and end cap RTE 25$m$, 25$c$, using two or more tethers 70$_1$, 70$_2$. In some embodiments, as shown in FIG. 9B, two RTE assemblies 25$a$ with respective at least one tether and collar can be used on a single cylinder 20. The collars 60$_1$, 60$_2$ can reside in abutting contact and the respective tethers 70₁, 70₁ can attach to different RTEs 25 (shown as 25m and 25c, for example).

FIG. 7A illustrates a sequence of steps that can be used to position the assembly 25a onto the cylinder 20. As shown, first (1) the assembly 25a is aligned with the cylinder so that the collar 60 slides onto the tapered forward end of the cylinder. Next (2), the collar 60 (with the RTE 25 attached and able to be move side to side relative to the cylinder while attached to the tether 70) is slid back to reside adjacent the fluid line junction 40j. Then (3) the RTE 25 can be attached to the rear end of the cylinder 20. The RTE 25 is then tethered to the collar 60 and the fluid junction provides a hard "stop" so that the RTE 25 remains attached to the collar 60 even if it becomes detached from the cylinder end.

FIG. 7B illustrates position (3), the use/implant configuration. FIG. 7B also illustrates the arcuate recesses 61 and the integral (moldably attached) configuration of the tether 70 to the collar 60 and/or the RTE 25.

FIGS. 7C and 7D illustrate a hoop-like collar 60 that can reside at an oblique angle with respect to the cylinder 20. As shown, a line drawn through a centerline 60t of the collar 60 can intersect the axial centerline 20c of the cylinder 20 typically at an angle α that is between about 10-75 degrees. The centerline 60t can be described as a transversely extending centerline as it is in a width dimension of the collar. This configuration may allow expansion of the cylinder 20 without exertion of compression onto the cylinder when in an expanded configuration.

FIG. 8 illustrates an alternate embodiment where the collar 60 is a two-piece collar 60a, 60b with two (substantially) circumferentially extending segments that can be attached about the cylinder 20 after it is in position proximate the fluid junction 40j to avoid the step of sliding the collar over the cylinder 20. The attachment can be a bayonet fit, snap-fit or other mechanical fastening configuration. Adhesive may be used but is not preferred.

As the RTEs 25 can be provided in different lengths, the collars 60 or tethers 70 (or both) can be color-coded to represent a length of the RTE for facilitating physician size selection.

FIG. 10 illustrates that the tether 70' can be attached to the collar 60 and/or RTE 25 after the RTE size is selected, e.g., the devices can be provided as separate components that can be assembled by a clinician prior to implantation of the device. The tether 70' can be attached to attachment members on the respective collar 60 and RTE 25. In some embodiments, the tether 70', collar 60 and RTE 25 are all provided as separate components and the tether 70' is attached in situ. In some embodiments, the collar and tether 60, 70 are provided as an assembly that is attached to the RTE 25 when the RTE size is selected for a patient. In some embodiments, the tether 70' and RTE 25 are provided as an assembly that is then attached to the collar 60 proximate to or during a surgical preparation or the actual surgery, typically after the collar 60 is in position on the cylinder 20.

Figure 12:
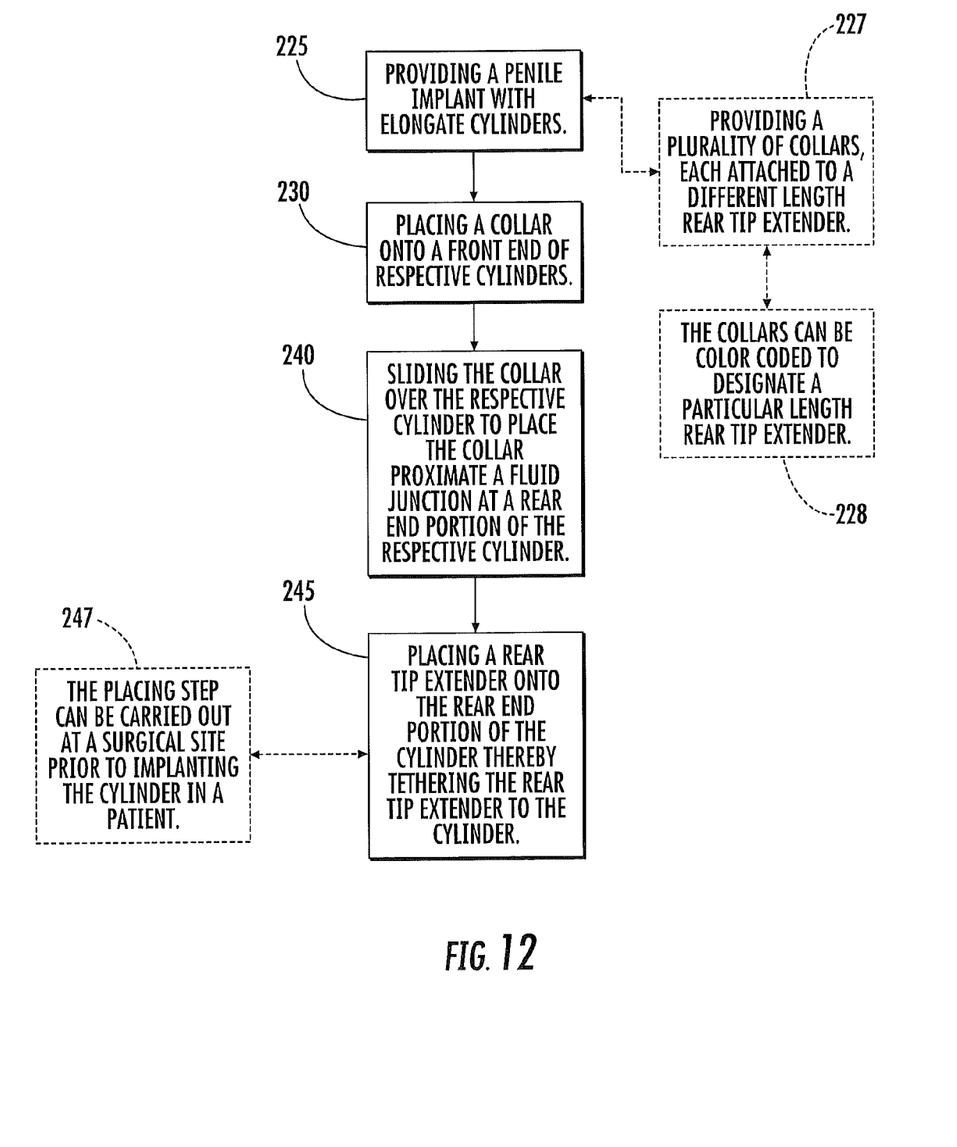
FIG. 12 is a flow chart of exemplary operations or actions that can be carried out to assemble an RTE assembly according to embodiments of the present invention.

FIG. 12 is a flow chart of exemplary operations that can be used to carry out embodiments of the present invention: The method can include: providing a penile implant with elongate cylinders (block 225); placing a collar onto a front end of respective cylinders (block 230); sliding the collars over the respective cylinder to place the collar proximate a fluid junction at a rear end portion of the respective cylinder (block 240); then, placing a rear tip extender onto the rear end portion of the cylinder thereby tethering the rear tip extender to the cylinder (block 245).

The method may optionally include providing a plurality of collars, each attached to a different length rear tip extender (block 227). The collars can be color-coded to designate a particular length rear tip extender (block 228).

The placing steps can be carried out at a surgical site prior to implanting the cylinder in a patient (block 247).

Figure 13:
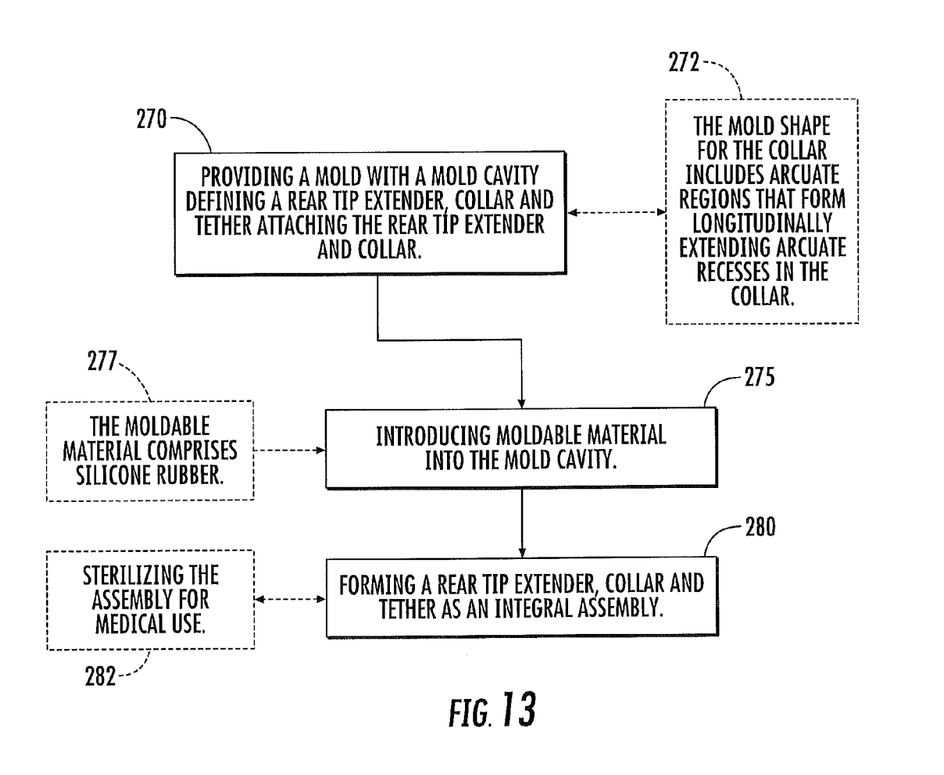
FIG. 13 is a flow chart of an exemplary fabrication process for an RTE assembly according to embodiments of the present invention.

FIG. 13 is a flow chart of exemplary steps of fabrication methods for fabricating an RTE assembly according to embodiments of the present invention. A mold is provided, the mold having a mold cavity defining a rear tip extender, collar and tether attaching the rear tip extender and collar (block 270). Moldable material is introduced into the mold cavity (block 275). A rear tip extender, collar and tether are formed as an integral (molded) assembly (block 280).

The mold shape for the collar can include arcuate regions that form longitudinally extending arcuate recesses in the collar (block 272). The moldable material can include (or be made totally of) silicone rubber (block 277).

The method can include sterilizing the assembly for medical use (block 282).

Figure 14A:
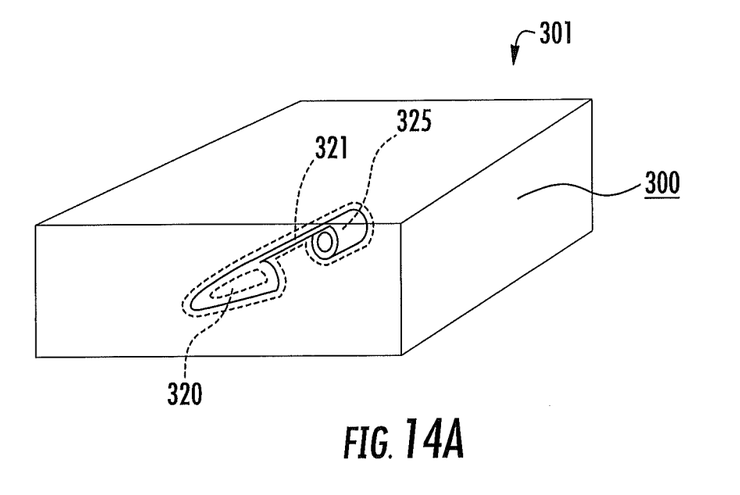
FIG. 14A is a schematic perspective view of an exemplary mold for an integral RTE assembly according to embodiments of the present invention.
Figure 14B:
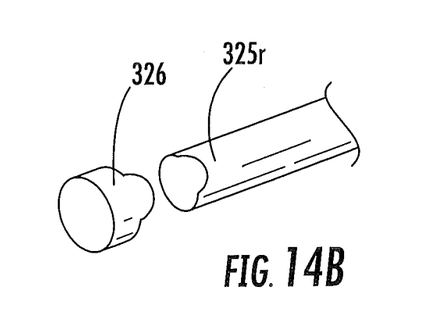
FIG. 14B is a schematic perspective view of an exemplary set of core rods that may be used to form a tethered RTE according to embodiment of the present invention.

FIG. 14A is a schematic illustration of a mold 300 that has a mold cavity 301 with a cavity shape and internal mold members 320, 321, 325 that form an integral RTE 25, collar 60 and tether 70 attached to both according to embodiments of the present invention. The mold 300 can be for injection molding or blow molding, for example. FIG. 14B illustrates cooperating core rods 325r, 326 with shapes that can form the collar with arcuate recess according to some embodiments of the present invention.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A rear tip extender assembly for a penile prosthesis implant, comprising:
    a rear tip extender sized and configured to attach to an end portion of an elongate cylinder of a penile prosthesis implant;
    a collar that is sized and configured to reside against an outer surface of the cylinder; and
    at least one tether that is attached to the rear tip extender and the collar, wherein the collar is loosely held on the cylinder with an inner diameter that is between 10-50% greater than an outer diameter of the cylinder and/or is configured to expand when the cylinder expands due to inflation.

2. The rear tip extender assembly of claim 1, wherein the rear tip extender comprises a rear tip cap with a closed end.

3. The rear tip extender assembly of claim 2, wherein the rear tip cap comprises silicone rubber.

4. The rear tip extender assembly of claim 1, wherein the collar and rear tip extender comprise an elastomeric material and the tether is moldably attached to at least one of the collar and rear tip extender.

5. The rear tip extender of claim 4, wherein the tether is moldably attached to both the collar and rear tip extender.

6. The rear tip extender assembly of claim 1, wherein the collar is sized and configured to slidably travel over a forward end of the cylinder and reside in front of a fluid line that extends outward from a rear portion of the cylinder.

7. The rear tip extender assembly of claim 1, in combination with a second rear tip extender assembly, wherein the rear tip assembly of claim 1 is a first rear tip extender assembly, the second rear tip extender assembly comprising:
a second rear tip extender sized and configured to attach to the end portion of the elongate cylinder of the penile prosthesis implant;
a second collar that is sized and configured to reside against the outer surface of the cylinder; and
at least one second tether that is attached to the second rear tip extender and the second collar,
wherein the second rear tip extender has a shorter or longer length than the rear tip extender of the first rear tip extender assembly and is interchangeably serially attachable to the end portion of the elongate cylinder of the penile prosthesis implant, and wherein the second collar and/or second tether has a different color than the collar and/or tether of the first rear tip extender assembly, the color corresponding to the length of the second rear tip extender.

8. The rear tip assembly of claim 1, wherein the tether extends in an orientation that is parallel to the cylinder for a distance between 0.5 inches and 5 inches between the collar and the rear tip extender.

9. The rear tip assembly of claim 1, wherein the tether is directly attached to the rear tip extender.

10. A penile prosthesis implant, comprising:
an elongate cylinder having longitudinally opposing front and rear end portions, the rear end portion comprising a fluid conduit junction;
a collar on the cylinder residing in front of the fluid conduit junction;
a rear tip extender attached to the rear end portion of the cylinder; and
at least one tether attached to the collar and the rear tip extender,
wherein the collar is loosely held on the cylinder with an inner diameter that is between 10-50% greater than an outer diameter of the cylinder.

11. The implant of claim 10, wherein the rear tip extender comprises a rear tip cap with a closed end.

12. The implant of claim 10, wherein the rear tip extender and the at least one tether comprises silicone rubber.

13. The implant of claim 10, wherein the collar and the rear tip extender comprise an elastomeric material and the at least one tether is moldably attached to the collar, the rear tip extender or both the collar and the rear tip extender.

14. The implant of claim 13, wherein the at least one tether is a single tether that is moldably attached to both the collar and the rear tip extender.

15. The implant of claim 10, wherein the collar is sized and configured to slidably travel over a forward end of the cylinder to reside adjacent the fluid conduit junction.

16. The implant of claim 10, wherein the tether extends between the collar and the rear tip extender in an orientation that is parallel to the cylinder.

17. The implant of claim 10, wherein the tether is directly attached to the rear tip extender.

18. A method of configuring a penile prosthesis implant for insertion into a patient, comprising:
providing a pair of elongate cylinders with longitudinally opposing front and rear end portions, the rear end portions having a fluid junction with a fluid line extending away from the cylinder;
sliding a collar having a longitudinally extending tether attached to a rear tip extender over the front end portion of each respective cylinder to a position adjacent the fluid junction; and
placing the rear tip extender on the rear end of the cylinder with the collar remaining positioned adjacent the fluid junction of the cylinder thereby tethering the rear tip extender to the collar on the cylinder, wherein the collar is loosely held on the cylinder with an inner diameter that is between 10-50% greater than an outer diameter of the cylinder and/or wherein the collar is configured to expand when the cylinder expands due to inflation.

19. The method of claim 18, further comprising providing instructional media showing the sliding and placing actions.

20. A rear tip extender assembly for a penile prosthesis implant, comprising:
a rear tip extender sized and configured to attach to an end portion of an elongate cylinder of a penile prosthesis implant;
a collar that is sized and configured to reside against an outer surface of the cylinder; and
at least one tether that is attached to the rear tip extender and the collar,
wherein the collar comprises at least one arcuate longitudinally extending recess.

21. A rear tip extender assembly for a penile prosthesis implant, comprising:
a rear tip extender sized and configured to attach to an end portion of an elongate cylinder of a penile prosthesis implant;
a collar that is sized and configured to reside against an outer surface of the cylinder; and
at least one tether that is attached to the rear tip extender and the collar,
wherein the collar comprises a plurality of circumferentially spaced apart arcuate recesses.

22. A penile prosthesis implant, comprising:
an elongate cylinder having longitudinally opposing front and rear end portions, the rear end portion comprising a fluid conduit junction;
a collar on the cylinder residing in front of the fluid conduit junction;
a rear tip extender attached to the rear end portion of the cylinder; and
at least one tether attached to the collar and the rear tip extender,
wherein the collar comprises at least one arcuate longitudinally extending recess.

23. A penile prosthesis implant, comprising:
an elongate cylinder having longitudinally opposing front and rear end portions, the rear end portion comprising a fluid conduit junction;
a collar on the cylinder residing in front of the fluid conduit junction;
a rear tip extender attached to the rear end portion of the cylinder; and
at least one tether attached to the collar and the rear tip extender, wherein the collar has a cross-sectional width that is between about 10-50% larger than a diameter of the cylinder, and wherein the collar resides with a transversely extending centerline thereof offset relative to an axially extending centerline of the cylinder.

24. A penile prosthesis implant, comprising:

an elongate cylinder having longitudinally opposing front and rear end portions, the rear end portion comprising a fluid conduit junction;

a collar on the cylinder residing in front of the fluid conduit junction;

a rear tip extender attached to the rear end portion of the cylinder; and at least one tether attached to the collar and the rear tip extender, wherein the collar is configured to expand when the cylinder expands due to inflation.

* * * * *